US011884799B2

(12) United States Patent
Nakao et al.

(10) Patent No.: US 11,884,799 B2
(45) Date of Patent: Jan. 30, 2024

(54) POLYETHYLENE RESIN COMPOSITION, LAMINATE, AND MEDICAL CONTAINER

(71) Applicant: TOSOH CORPORATION, Shunan (JP)

(72) Inventors: Hideyasu Nakao, Yokkaichi (JP); Yoshiyuki Moro, Yokkaichi (JP)

(73) Assignee: TOSOH CORPORATION, Shunan (JP)

( * ) Notice: Subject to any disclaimer, the term of this patent is extended or adjusted under 35 U.S.C. 154(b) by 553 days.

(21) Appl. No.: 17/267,942

(22) PCT Filed: Sep. 6, 2019

(86) PCT No.: PCT/JP2019/035130
§ 371 (c)(1),
(2) Date: Feb. 11, 2021

(87) PCT Pub. No.: WO2020/054594
PCT Pub. Date: Mar. 19, 2020

(65) Prior Publication Data
US 2021/0214538 A1   Jul. 15, 2021

(30) Foreign Application Priority Data

Sep. 12, 2018 (JP) ................... 2018-170650

(51) Int. Cl.
| | |
|---|---|
| *C08L 23/06* | (2006.01) |
| *A61J 1/10* | (2006.01) |
| *A61J 1/14* | (2023.01) |
| *B32B 1/02* | (2006.01) |
| *B32B 27/08* | (2006.01) |
| *B32B 27/18* | (2006.01) |
| *B32B 27/32* | (2006.01) |
| *C08L 23/08* | (2006.01) |
| *C08F 210/16* | (2006.01) |
| *C08F 4/659* | (2006.01) |
| *C08F 4/6592* | (2006.01) |
| *B32B 27/20* | (2006.01) |

(Continued)

(52) U.S. Cl.
CPC ............... *C08L 23/06* (2013.01); *A61J 1/10* (2013.01); *A61J 1/1468* (2015.05); *B32B 1/02* (2013.01); *B32B 27/08* (2013.01); *B32B 27/18* (2013.01); *B32B 27/32* (2013.01); *C08F 210/16* (2013.01); *C08L 23/0815* (2013.01); *A61L 31/048* (2013.01); *B32B 7/12* (2013.01); *B32B 27/20* (2013.01); *B32B 2250/03* (2013.01); *B32B 2250/242* (2013.01); *B32B 2250/40* (2013.01); *B32B 2270/00* (2013.01); *B32B 2307/306* (2013.01); *B32B 2307/412* (2013.01); *B32B 2307/7242* (2013.01); *B32B 2307/732* (2013.01); *B32B 2439/46* (2013.01); *B32B 2439/80* (2013.01); *C08F 4/65912* (2013.01); *C08F 4/65916* (2013.01); *C08F 4/65925* (2013.01); *C08F 4/65927* (2013.01); *C08F 2410/06* (2021.01); *C08L 2205/025* (2013.01); *C08L 2205/03* (2013.01); *C08L 2207/062* (2013.01); *C08L 2207/066* (2013.01)

(58) Field of Classification Search
CPC . A61J 1/10; A61J 1/1468; A61L 31/04; A61L 31/048; C08F 4/65916; C08F 4/65927; C08F 4/65912; C08F 4/65925; C08F 210/16; C08F 2410/06; C08L 23/06; C08L 23/0815; C08L 2205/025; C08L 2205/03; C08L 2207/062; C08L 2207/066; B32B 1/02; B32B 7/12; B32B 27/08; B32B 27/18; B32B 27/20; B32B 28/32; B32B 2250/03; B32B 2250/242; B32B 2250/40; B32B 2270/00; B32B 2439/80; B32B 2307/306; B32B 2307/412; B32B 2307/7242; B32B 2307/732; B32B 2439/46
See application file for complete search history.

(56) References Cited

U.S. PATENT DOCUMENTS

| | | | |
|---|---|---|---|
| 2015/0225554 A1 | 8/2015 | Iwasaki et al. | |
| 2016/0237263 A1 | 8/2016 | Tsuruta et al. | |

(Continued)

FOREIGN PATENT DOCUMENTS

| | | |
|---|---|---|
| CN | 101575430 A | 11/2009 |
| CN | 104428361 A | 3/2015 |
| CN | 105612208 A | 5/2016 |

(Continued)

OTHER PUBLICATIONS

International Search Report for PCT/JP2019/035130, dated Dec. 3, 2019.

(Continued)

*Primary Examiner* — John Kim
(74) *Attorney, Agent, or Firm* — Sughrue Mion, PLLC

(57) ABSTRACT

A polyethylene resin composition comprising from 50 to 89 parts by weight of a linear low density polyethylene (A) having specific physical properties, from 10 to 40 parts by weight of a high density polyethylene (B) having specific physical properties, and from 1 to 20 parts by weight of a high pressure low density polyethylene (C) having specific physical properties (the total amount of (A), (B) and (C) is 100 parts by weight), and having MFR of from 3.0 to 9.0 g/10 min, is excellent in heat resistance, flexibility, barrier property and cleanness (low particle property), will not deform even after sterilization at 121° C., maintains high transparency and is excellent in processability in water cooling blown-film extrusion, and a medical container using it.

7 Claims, No Drawings

(51) Int. Cl.
 *B32B 7/12* (2006.01)
 *A61L 31/04* (2006.01)

(56) References Cited

U.S. PATENT DOCUMENTS

2017/0197769 A1 7/2017 Unai et al.
2017/0341354 A1 11/2017 Sekiya et al.

FOREIGN PATENT DOCUMENTS

| | | | |
|---|---|---|---|
| CN | 106457805 | A | 2/2017 |
| CN | 107107596 | A | 8/2017 |
| EP | 2 889 328 | A1 | 7/2015 |
| JP | 07-125738 | A | 5/1995 |
| JP | 08-244791 | A | 9/1996 |
| JP | 08-309939 | A | 11/1996 |
| JP | 2002-265705 | A | 9/2002 |
| JP | 2005-007888 | A | 1/2005 |
| JP | 2008-018063 | A | 1/2008 |
| JP | 2014-040545 | A | 3/2014 |
| JP | 10-2015-0018624 | A | 2/2015 |
| JP | 2015-042557 | A | 3/2015 |
| JP | 2015-074744 | A | 4/2015 |
| JP | 2017-186499 | A | 10/2017 |
| WO | 2014/030642 | A1 | 2/2014 |

OTHER PUBLICATIONS

International Preliminary Report on Patentability dated Mar. 9, 2021, with attached English translation of Written Opiniion (PCT/ISA/237) in International Application No. PCT/JP2019/035130.

POLYETHYLENE RESIN COMPOSITION, LAMINATE, AND MEDICAL CONTAINER

CROSS REFERENCE TO RELATED APPLICATIONS

This application is a National Stage of International Application No. PCT/JP2019/035130 filed Sep. 6, 2019, claiming priority based on Japanese Patent Application No. 2018-170650 filed Sep. 12, 2018, the entire contents of which are incorporated by reference herein.

TECHNICAL FIELD

The present invention relates to a polyethylene resin composition and a laminate using it, and a medical container using it. More particularly, it relates to a resin composition excellent in extrusion property and forming stability at the time of water cooling blown-film extrusion. Further, it relates to a laminate formed of the resin composition, suitable for a medical container to store a medicinal solution, blood, etc., such as an infusion solution bag, and a medical container using it.

BACKGROUND ART

A medical container to store a medicinal solution, blood, etc. is required to have transparency to confirm inclusion of foreign matters and changes by blending of chemical agents, flexibility to make the medicinal solution be easily discharged, gas barrier property to suppress degeneration or a decrease in quality of the medicinal solution, etc. by infiltration of water vapor or oxygen into the container, and to have suppressed elution of fine particles from the container (low particle property). Further, a product having a content stored in such a container is commonly subjected to heat sterilization. Particularly the infusion solution, etc. to be directly administered to the blood is strictly required to be in an asepsis condition, and thus high temperature sterilization is becoming common in recent years as international standard, and heat resistance to withstand sterilization at 121° C. is strongly desired.

Heretofore, as such a medical container, a glass container has been used, however, due to problems such as breakage of the container by impact or falling, and contamination by infiltration of the air into the container at the time of administration of the medicinal solution, a plastic container excellent in impact resistance, being flexible and capable of easily discharging the content, has been used. As such a plastic container, a flexible vinyl chloride resin, an ethylene/vinyl acetate copolymer resin, a polypropylene resin, and a polyethylene resin such as a high pressure low density polyethylene, a linear low density polyethylene or a high density polyethylene has been used. However, a flexible vinyl chloride resin from which the plasticizer is eluted into the medicinal solution is problematic in view of hygiene, and an ethylene/vinyl acetate copolymer resin is inferior in heat resistance. As a material of a container which satisfies transparency and heat resistance as mentioned above, polypropylene has been widely used, however, polypropylene has tertiary carbon atoms repeatedly and is intrinsically likely to undergo oxidative degradation, and thus addition of an antioxidant is essential. In recent years, since safety requirement is increasing, particularly for a medical container for a medicinal solution, an additive-free clean material is preferred. Accordingly, development of a new medical container which has both transparency and heat resistance using an additive-free material which replaces polypropylene has been desired. Further, a polyethylene resin also has problems such that if the density is decreased to satisfy transparency and flexibility, heat resistance will decrease, and if the density is increased to satisfy heat resistance, transparency and flexibility will decrease.

In recent years, a linear polyethylene produced with a single site catalyst excellent in transparency is developed, and a method to solve the above problems by laminating a film made of such a polyethylene has been proposed (Patent Documents 1 to 3). However, such a laminate is still insufficient in transparency, the impact strength of the heat sealed portion of a container formed of such a laminate is not necessarily sufficient, and improvement has been desired.

Under the above circumstances, in order to produce a polyethylene container which satisfies both transparency and heat resistance, a resin composition containing polyethylene as the main component, a multilayer container, and a polyethylene resin having specific physical properties, have been proposed (for example, Patent Documents 4 to 7). Further, the present inventors have found that by using a polyethylene resin composition having a polyethylene resin having specific physical properties blended in a specific amount, a medical container excellent in transparency, heat resistance and cleanness can be provided (for example, Patent Document 8).

However, if an operator which has used polypropylene is to change the material to the above polyethylene resin to improve cleanness, a forming machine designed for polypropylene has a narrow flow path inside the die, thus increasing the resin pressure, and thus disturbing the balance in the flow rate at the respective portions and thus making film thickness be non-uniform in the width direction, whereby forming may sometimes be difficult. If the viscosity of the polyethylene resin is decreased to lower the resin pressure, the melt strength decreases, whereby bubble non-uniformity tends to be significant, and draw resonance may occur, thus decreasing forming stability. Accordingly, a clean polyethylene resin which can be stably produced even with a forming machine for polypropylene, while having heat resistance and transparency required for a medical container, has been desired.

PRIOR ART DOCUMENTS

Patent Documents

Patent Document 1: JP-A-H08-309939
Patent Document 2: JP-A-H07-125738
Patent Document 3: JP-A-H08-244791
Patent Document 4: JP-A-2002-265705
Patent Document 5: JP-A-2005-7888
Patent Document 6: JP-A-2015-42557
Patent Document 7: JP-A-2008-18063
Patent Document 8: JP-A-2015-74744

DISCLOSURE OF INVENTION

Technical Problem

It is an object of the present invention to provide a polyethylene resin composition which is excellent in heat resistance, flexibility, barrier property and cleanness (low particle property), which are hardly satisfied at the same time by a conventional resin for a medical container, which will not deform even after sterilization at 121° C., which maintains high transparency and which is excellent in processability in water cooling blown-film extrusion, and a medical container using it.

Solution to Problem

The present inventors have conducted extensive studies and as a result, found that the above object can be achieved by using a resin composition comprising a polyethylene resin having specific physical properties blended in a specific amount, and accomplished the present invention.

That is, the present invention resides in the following [1] to [7].

[1] A polyethylene resin composition for a medical container, comprising from 50 to 89 parts by weight of a linear low density polyethylene (A) which satisfies the following requirements (a) to (c), from 10 to 40 parts by weight of a high density polyethylene (B) which satisfies the following requirements (d) to (f), and from 1 to 20 parts by weight of a high pressure low density polyethylene (C) which satisfies the following requirements (g) to (i) (the total amount of (A), (B) and (C) is 100 parts by weight), and the polyethylene resin composition satisfying the following requirement (j):

(a): the density is from 890 to 920 kg/m$^3$,
(b): the melt mass flow rate (hereinafter referred to as MFR) measured in accordance with JIS K6922-1 at 190° C. under a load of 21.18 N is from 3.0 to 15 g/10 min,
(c): the ratio of the weight average molecular weight (Mw) to the number average molecular weight (Mn) (Mw/Mn) is from 2.0 to 3.0,
(d): the density is from 935 to 970 kg/m$^3$,
(e): MFR is from 3.0 to 15 g/10 min,
(f): the ratio of the weight average molecular weight (Mw) to the number average molecular weight (Mn) (Mw/Mn) is from 2.0 to 3.0,
(g): the density is from 910 to 930 kg/m$^3$,
(h): MFR is from 0.1 to 1.0 g/10 min,
(i): the melt strength is from 200 to 400 mN,
(j): MFR is from 3.0 to 9.0 g/10 min.

[2] A laminate of at least three layers comprising at least layer A, layer B and layer C in this order, wherein the layer B is formed of the polyethylene resin composition as defined in the above [1], and the layers A and C are formed of a thermoplastic resin.
[3] The laminate according to the above [1] or [2], wherein the thermoplastic resin for the layers A and C is a resin composition containing polyethylene.
[4] The laminate according to the above [2] or [3], which has a light transmittance of at least 70% after sterilized at 121° C.
[5] A medical container comprising the laminate as defined in any one of the above [2] to [4].
[6] A medical container comprising a compartment to store a medicinal solution, wherein at least the compartment comprises the laminate as defined in any one of the above [2] to [4].
[7] The medical container according to the above [5] or [6], which has a light transmittance of at least 70% after subjected to sterilization at 121° C. for 20 minutes.

Now, the polyethylene resin according to the present invention, the resin composition comprising it, the laminate of the present invention, and a medical container comprising it, will be described.

(1) Linear low density polyethylene (A)

The linear low density polyethylene (A) used in the present invention is a copolymer of ethylene and an α-olefin.

The linear low density polyethylene (A) of the present invention has a melt flow rate as measured in accordance with JIS K6922-1 at 190° C. under a load of 21.18 N of from 3.0 to 15 g/10 min, preferably from 3.0 to 10 g/10 min, more preferably from 4.0 to 7.0 g/10 min. If MFR is less than 3.0 g/10 min, the load on the extruder tends to be heavy at the time of forming and in addition, the thickness tends to be uneven in the width direction at the time of forming. Further, if MFR exceeds 15 g/10 min, the forming stability tends to decrease.

Of the linear low density polyethylene (A) of the present invention, the density in accordance with JIS K6922-1 is from 890 to 920 kg/m$^3$, preferably from 900 to 910 kg/m$^3$. If the density is less than 890 kg/m$^3$, the heat resistance may be insufficient so that the container may deform by 121° C. sterilization, and if it exceeds 920 kg/m$^3$, transparency and flexibility tend to decrease.

Of the linear low density polyethylene (A) of the present invention, the ratio of the weight average molecular weight (Mw) to the number average molecular weight (Mn) (Mw/Mn) is from 2.0 to 3.0. When Mw/Mn is at most 3.0, the decrease in transparency when the obtained laminate is subjected to sterilization at 121° C. tends to be small, and high strength will be obtained. When Mw/Mn is at least 2.0, the extrusion load at the time of forming can be suppressed.

The linear low density polyethylene (A) of the present invention may be produced, for example, by a production method such as high pressure method, solution method or vapor-phase method, by the method as disclosed in JP-A-2009-275059 or JP-A-2013-81494, by copolymerizing ethylene and an α-olefin by a metallocene catalyst comprising an organic transition metal compound containing a cyclopentadienyl derivative and a compound and/or an organic metal compound which reacts with it to form an ionic complex.

The α-olefin may be one commonly called an α-olefin, and is preferably a 03.12 α-olefin such as propylene, butene-1, hexene-1, octene-1 or 4-methyl-1-pentene. The copolymer of ethylene and an α-olefin may, for example, be an ethylene/hexene-1 copolymer, an ethylene/butene-1 copolymer or an ethylene/octene-1 copolymer.

(2) High density polyethylene (B)

The high density polyethylene (B) used in the present invention is an ethylene homopolymer or a copolymer of ethylene and an α-olefin.

The high density polyethylene (B) of the present invention has MFR as measured in accordance with JIB K6922-1 at 190° C. under a load of 21.18 N of from 3.0 to 15 g/10 min, preferably from 3.0 to 10 g/10 min, more preferably from 4.0 to 6.0 g/10 min. If MFR is less than 3.0 V 0 min, the load on the extruder tends to be heavy at the time of forming, in addition, the thickness tends to be uneven in the width direction at the time of forming. Further, if MFR exceeds 15 g/10 min, the melt strength tends to be low, and the forming stability tends to decrease.

Of the high density polyethylene (B) of the present invention, the density in accordance with JIS K6922-1 is from 935 to 970 kg/m$^3$, preferably from 950 to 960 kg/m$^3$. If the density is less than 935 kg/m$^3$, the heat resistance may be insufficient so that the container may deform by 121° C. sterilization, and if it exceeds 970 kg/m$^3$, transparency and flexibility tend to decrease.

Of the high density polyethylene (B) of the present invention, the ratio of the weight average molecular weight (Mw) to the number average molecular weight (Mn) (Mw/Mn) is from 2.0 to 3.0. When Mw/Mn is at most 3.0, the decrease in transparency when the obtained laminate is subjected to sterilization at 121° C. tends to be small. When Mw/Mn is at least 2.0, the extrusion load at the time of forming can be suppressed.

The high density polyethylene (B) of the present invention may be produced, for example, by a production method such as slurry method, solution method or vapor-phase method, by the method as disclosed in JP-A-2009-275059 or JP-A-2013-81494, by homopolymerizing ethylene or copolymerizing ethylene and an α-olefin by a metallocene catalyst comprising an organic transition metal compound containing a cyclopentadienyl derivative and a compound and/or an organic metal compound which reacts with it to form an ionic complex.

The α-olefin may be one commonly called an α-olefin, and is preferably a 03_12 α-olefin such as propylene, butene-1, hexene-1, octene-1 or 4-methyl-1-pentene. The copolymer of ethylene and an α-olefin may, for example, be an ethylene/hexene-1 copolymer, an ethylene/butene-1 copolymer or an ethylene/octene-1 copolymer.

(3) High pressure low density polyethylene (C)

The high pressure low density polyethylene (C) of the present invention has a melt flow rate (hereinafter referred to as MFR) as measured in accordance with JIS K6922-1 at 190° C. under a load of 21.18 N of from 0.1 to 1.0 g/10 min, preferably from 0.1 to 0.5 g/10 min, more preferably from 0.2 to 0.4 g/10 min. If MFR is less than 0.1 g/10 min, the load on the extruder tends to be heavy at the time of forming, in addition, the viscosity difference with other materials tends to be significant, thus forming fisheyes. Further, if MFR exceeds 1.0 g/10 min, forming stability tends to decrease.

Of the high pressure low density polyethylene (C) of the present invention, the density in accordance with JIB K6922-1 is from 910 to 930 kg/m$^3$, preferably from 915 to 925 kg/m$^3$, more preferably from 918 to 922 kg/m$^3$. If the density is less than 910 kg/m$^3$, the heat resistance may be insufficient so that the container may deform by 121° C. sterilization, and if it exceeds 930 kg/m$^3$, transparency and flexibility tend to decrease.

The high pressure low density polyethylene (C) of the present invention has a melt strength of from 200 to 400 mN, preferably from 220 to 350 mN, more preferably from 250 to 300 mN. If the melt strength is less than 200 mN, forming stability tends to decrease. If the melt strength exceeds 400 mN, film drawbacks may occur if the drawing rate is increased.

The high pressure low density polyethylene (C) of the present invention may be available as a commercial product, for example, PETROTHENE 172 (trade name) manufactured by TOSOH CORPORATION.

(4) Polyethylene resin composition

The polyethylene resin composition according to an embodiment of the present invention may be obtained by a method of mixing the linear low density polyethylene (A), the high density polyethylene (B) and the high pressure low density polyethylene (C) by a conventional method, for example, by a Henschel mixer, a V-blender, a ribbon blender or a tumbler blender, or by further melt-kneading a mixture obtained by such a method by e.g. a single screw extruder, a twin screw extruder, a kneader or a Banbury mixer, followed by granulation.

The blend ratio of the linear low density polyethylene (A), the high density polyethylene (B) and the high pressure low density polyethylene (C) of the resin composition of the present invention is preferably such that the amount of the linear low density polyethylene (A) is from 50 to 89 parts by weight, preferably from 60 to 80 parts by weight, more preferably from 65 to 75 parts by weight, the amount of the high density polyethylene (B) is from 10 to 40 parts by weight, preferably from 15 to 35 parts by weight, more preferably from 15 to 30 parts by weight, and the amount of the high pressure low density polyethylene (C) is from 1 to 20 parts by weight, preferably from 2 to 15 parts by weight, more preferably from 3 to 10 parts by weight. The total amount of (A), (B) and (C) is 100 parts by weight.

If the amount of the linear low density polyethylene (A) is less than 50 parts by weight, transparency, flexibility and strength of the obtained laminate tend to decrease. If the amount of the linear low density polyethylene (A) exceeds 89 parts by weight, forming stability tends to decrease, and heat resistance of the obtained laminate tends to decrease.

If the amount of the high density polyethylene (B) is less than 10 parts by weight, heat resistance of the obtained laminate tends to decrease, thus leading to deformation and a decrease in transparency of a container after subjected to sterilization at 121° C. If the amount of the high density polyethylene (B) exceeds 40 parts by weight, flexibility, transparency and strength of the obtained laminate tend to decrease.

If the amount of the low density polyethylene (C) is less than 1 part by weight, forming stability at the time of water cooling blown-film extrusion tends to decrease, whereby the laminate can not be stably produced. If the amount of the low density polyethylene (C) exceeds 20 parts by weight, transparency, heat resistance and strength of the obtained laminate tend to decrease.

The resin composition of the present invention preferably has MFR of from 3.0 to 9.0 g/10 min and a density of from 910 to 925 kg/m$^3$, whereby forming stability is good, and transparency after sterilization at 121° C. is particularly excellent, and more preferably MFR of from 3.0 to 5.0 g/10 min and a density of from 910 to 920 kg/m$^3$. If MFR is less than 3.0, extrusion property tends to decrease, and if MFR exceeds 9.0, forming stability and strength tend to decrease.

In the polyethylene resin composition of the present invention, within a range not to remarkably impair the effects of the present invention, a commonly used known additive such as an antioxidant, an antistatic agent, a lubricant, an anti-blocking agent, an anti-fogging agent, an organic or inorganic pigment, an ultraviolet absorber or a dispersing agent, may be blended as the case requires. The method of blending the above additive in the resin composition of the present invention is not particularly limited, and a method of directly adding the additive in a pellet granulation step after polymerization, or a method of preliminarily preparing a high concentration master batch, and dry-blending it at the time of forming, may be mentioned.

Further, in the polyethylene resin composition of the present invention, within a range not to impair the effects of the present invention, other thermoplastic resin such as a polypropylene, an ethylene/propylene copolymer rubber or poly-1-butene may be blended.

(5) Laminate

The laminate according to an embodiment of the present invention is a laminate of at least three layers comprising at least layer A, layer B and layer C in this order, wherein the layer B is formed of the following polyethylene resin composition, and the layers A and C are formed of a thermoplastic resin.

A polyethylene resin composition comprising from 50 to 89 parts by weight of a linear low density polyethylene (A)

which satisfies the following requirements (a) to (c), from 10 to 40 parts by weight of a high density polyethylene (B) which satisfies the following requirements (d) to (f), and from 1 to 20 parts by weight of a high pressure low density polyethylene (C) which satisfies the following requirements (g) to (i) (the total amount of (A), (B) and (C) is 100 parts by weight), and the polyethylene resin composition satisfying the following requirement (j):

(a): the density is from 890 to 920 kg/m$^3$,
(b): MFR is from 3.0 to 15 g/10 min,
(c): the ratio of the weight average molecular weight (Mw) to the number average molecular weight (Mn) (Mw/Mn) is from 2.0 to 3.0,
(d): the density is from 935 to 970 kg/m$^3$,
(e): MFR is from 3.0 to 15 g/10 min,
(f): the ratio of the weight average molecular weight (Mw) to the number average molecular weight (Mn) (Mw/Mn) is from 2.0 to 3.0,
(g): the density is from 910 to 930 kg/m$^3$,
(h): MFR is from 0.1 to 1.0 g(10 min,
(i): the melt strength is from 200 to 400 mN,
(j): MFR is from 3.0 to 9.0 g/10 min, The thermoplastic resin to be used for the layer A and the layer C of the laminate of the present invention is not particularly limited, and is preferably a resin excellent in the balance between transparency and heat resistance. It may, for example, be a resin composition containing polyethylene, and the polyethylene is suitably Nipolon-P FY13, Nipolon-P FY11 (trade names), etc. manufactured by TOSOH CORPORATION, in view of hygiene, transparency and heat resistance. Further, within a range not to impair the effects of the present invention, a resin other than polyethylene, such as polypropylene, may be used for the layer A or the layer C.

The laminate of the present invention is not particularly limited, so long as it has the layer A, the layer B and the layer C (the layer C is the heat seal layer) in this order, regarding the other layer structure. With respect to the number of the layers, a three-layer structure comprising layer A/layer B/layer C is most preferred, but the structure is not limited thereto, and a layer structure of layer A/layer B/center layer/layer B/layer C having a layer further interposed in the layer B in the layer structure of layer A/layer B/layer C may be employed, or other layer may optionally be interposed as the case requires between the layer A and the layer B, or between the layer B and the layer C. Such other layer may, for example, be an adhesive layer, a gas barrier layer or an ultraviolet absorbing layer. For example, the layer structure may be a five-layer structure of layer A/gas barrier layer/layer B/adhesive layer/layer C. Otherwise, a new layer may further be provided outside the layer C. The symbol/between layers means the layers are adjacent to each other.

The adhesive constituting the adhesive layer may, for example, be a polyurethane adhesive, a vinyl acetate adhesive, a hot melt adhesive or an adhesive resin such as a maleic anhydride-modified polyolefin or an ionomer resin. In a case where an adhesive layer is included in the layer structure, essential constituting layers such as the outer layer, the intermediate layer and the inner layer are co-extruded with such an adhesive and laminated.

The entire thickness of the laminate in the present invention is not particularly limited and may optionally be determined as the case requires, and is preferably from 0.01 to 1 mm, more preferably from 0.1 to 0.5 mm.

The thickness ratio of the respective layers is not particularly limited, and it is preferred that the outer layer and the inner layer having an increased density to prevent deformation and fusion e.g. by sterilization are thinner, and the intermediate layer having a lowered density to increase transparency is thicker, whereby transparency and heat resistance will be well balanced. The thickness ratio of the layers is preferably at a level of layer A:layer B:layer C=1 to 30:40 to 98:1 to 30 (provided that the total is 100).

The laminate of the present invention preferably has a light transmittance of at least 70% after subjected to sterilization at 121° C. for 20 minutes for the viewpoint of transparency.

The method for producing the laminate of the present invention is not particularly limited ay may, for example, be a method for forming a multilayer film or sheet by water-cooling or air-cooling multilayer blown film co-extrusion method, co-extrusion multilayer T-die method, dry lamination method or extrusion lamination method. Among them, water cooling multilayer blown film co-extrusion method or co-extrusion multilayer T-die method is preferred. Particularly, water cooling multilayer blown film co-extrusion method is significantly advantageous in transparency, hygiene, etc.

(6) Medical container

The medical container according to an embodiment of the present invention comprises the laminate. The medical container of the present invention is a medical container comprising a compartment to store a medicinal solution, wherein at least the compartment comprises the above laminate.

The medical container of the present invention has a light transmittance of at least 70% after subjected to sterilization at 121° C. for 20 minutes for the viewpoint of transparency.

In a case where the laminate is formed into a film by water cooling multilayer blown film co-extrusion, two sheets of the obtained film may be overlaid, and the peripheral portion is heat-sealed to form a bag-form compartment. Otherwise, using the obtained film, by heating plate forming such as vacuum forming or pressure forming, a concave portion to be a compartment is formed, such films are overlaid so that the concave portions face each other, and the peripheral portion is heat-sealed to form a compartment. On that occasion, the port portion to be the inlet/outlet of a medicinal solution, may be formed by heat sealing simultaneously with formation of the compartment, or formation of the compartment and formation of the port portion may be carried out separately.

The polyethylene-made medical container of the present invention can be used for the medical field in general, for example, as a blood bag, a blood platelet storage bag, an infusion solution (medicinal solution) bag, a medical multi-chamber container or a dialysis bag.

Advantageous Effects of Invention

The resin composition of the present invention is excellent in forming stability at the time of water cooling blown film extrusion, and a laminate comprising it is excellent in transparency, flexibility, barrier property and cleanness (low particle property) and maintains transparency even after sterilization at 121° C., and is thereby suitably used for a medical container such as a medical infusion solution bag which is required to have high transparency and heat resistance.

EXAMPLES

Now, the present invention will be described in further detail with reference to Examples. However, it should be understood that the present invention is by no means restricted to such specific Examples.

A. Resin

Various properties of resins used for Examples and Comparative Examples were evaluated in accordance with the following methods.

<Density>

The density was measured by density gradient tube method in accordance with JIS K6922-1.

<MFR>

MFR (melt flow rate) was measured in accordance with JIS K6922-1.

<Molecular Weight, Molecular Weight Distribution>

The weight average molecular weight (Mw), the number average molecular weight (Mn), the ratio (Mw/Mn) of the weight average molecular weight to the number average molecular weight and the peak top molecular weight (Mp) were measured by GPO, using a GPC apparatus (manufactured by TOSOH CORPORATION, HLC-8121GPC/HT (trade name)) and a column (manufactured by TOSOH CORPORATION, TSKgel GMHhr-H(20)HT (trade name)), at a column temperature set at 140° C., using 1,2,4-trichlorobenzene as an eluent. The measurement sample was prepared at a concentration of 1.0 mg/ml, and 0.3 ml of the measurement sample was injected for measurement. The analytical curve of the molecular weight was calibrated using a polystyrene sample having a known molecular weight. Mw and Mn were obtained as values as calculated as linear polyethylene.

Melt Strength>

To measure the melt strength, to a capillary viscometer (manufactured by Toyo Seiki Seisaku-Sho, Ltd trade name: CAPILOGRAPH) having a barrel diameter of 9.55 mm, a die having a length of 8 mm and a diameter of 2.095 mm was set so that the entrance angle would be 90° for measurement. The temperature was set at 160° C., the piston descending speed was 10 mm/min, the draw ratio was set at 47, and the load (mN) required for drawing was taken as the melt strength. In a case where the maximum draw ratio was less than 47, the load (mN) required for drawing at the maximum draw ratio at which breaking did not occur was taken as the melt strength.

(1) Linear Low Density Polyethylene

LL-1

[Preparation of Modified Clay]

To 1,500 ml of water, 30 ml of 37% hydrochloric acid and 106 g of N,N-dirnethyl-behenylamine were added to prepare an aqueous N,N-dimethyl-behenyl ammonium hydrochloride solution. 300 g of montmorillonite having an average particle size of 7.8 μm (prepared by grinding KUNIPIA F, tradename, manufactured by KUNIMINE INDUSTRIES, CO., LTD. by a jet grinding machine) was added to the aqueous hydrochloride solution, followed by reaction for 6 hours. After completion of the reaction, the reaction solution was subjected to filtration, and the obtained cake was vacuum dried for 6 hours to obtain 370 g of modified clay compound. [Preparation of polymerization catalyst]

Into a 20 L stainless steel container in a nitrogen atmosphere, 3.3 L of heptane, a heptane solution (20 wt % diluted) of triethylalurninum in an amount of 1.13 mol (0.9 L) per aluminum atom, and 50 g of the above obtained modified clay compound were added, followed by stirring for one hour. Diphenylmethylene(4-phenyl-indenyl)(2,7-di-t-butyl-9-fluorenyl)zirconium dichloride was added thereto in an amount of 1.25 mmol per zirconium atom, followed by stirring for 12 hours. To the obtained suspension system. 5.8 L of an aliphatic saturated hydrocarbon solvent (manufactured by Idemitsu Petrochemical Co., Ltd., tradename: IP SOLVENT 2835) was added to prepare catalyst (zirconium concentration: 0.125 mmol/L).

[Production of LL-1]

Using a vessel type reactor equipped for high temperature high pressure polymerization, ethylene and 1-hexene were continuously injected into the reactor, and the total pressure was set at 90 MPa, the 1-hexene concentration at 18 mol % and the hydrogen concentration at 8 mol %. The content in the reactor was stirred at 1,500 rpm, the above obtained polymerization catalyst was continuously supplied from the supply port of the reactor, and polymerization reaction was carried out while the average temperature was kept at 200° C. The obtained linear low density polyethylene LL-1 had MFR=4.0 g/10 min and a density of 910 kg/m$^3$. The results of evaluation of basic properties of LL-1 are shown in Table 1.

LL-2

[Preparation of Modified Clay]

Modified clay compound was prepared in the same manner as for LL-1.

[Preparation of Polymerization Catalyst]

Polymerization catalyst was prepared in the same manner as for LL-1.

[Production of LL-2]

Using a vessel type reactor equipped for high temperature high pressure polymerization, ethylene and 1-hexene were continuously injected into the reactor, and the total pressure was set at 90 MPa, the 1-hexene concentration at 24 mol % and the hydrogen concentration at 6 mol %. The content in the reactor was stirred at 1,500 rpm, the above obtained polymerization catalyst was continuously supplied from the supply port of the reactor, and polymerization reaction was carried out while the average temperature was kept at 200° C. The obtained linear low density polyethylene LL-2 had MFR=5.0 g/10 min and a density of 900 kg/m$^3$. The results of evaluation of basic properties of LL-2 are shown in Table 1,

LL-3

[Preparation of Modified Clay]

Modified clay compound was prepared in the same manner as for LL-1.

[Preparation of Polymerization Catalyst]

Polymerization catalyst was prepared in the same manner as for LL-1.

[Production of LL-3]

Using a vessel type reactor equipped for high temperature high pressure polymerization, ethylene and 1-hexene were continuously injected into the reactor, and the total pressure was set at 90 MPa, the 1-hexene concentration at 19 mol % and the hydrogen concentration at 12 mol %, The content in the reactor was stirred at 1,500 rpm, the above obtained polymerization catalyst was continuously supplied from the supply port of the reactor, and polymerization reaction was carried out while the average temperature was kept at 200° C. The obtained linear low density polyethylene LL-3 had MFR=7.0 g/10 min and a density of 910 kg/m$^3$. The results of evaluation of basic properties of LL-3 are shown in Table 1.

LL-4

[Preparation of Modified Day]

Modified day compound was prepared in the same manner as for LL-1.

[Preparation of Polymerization Catalyst]

Polymerization catalyst was prepared in the same manner as for LL-1.

[Production of LL-4]

Using a vessel type reactor equipped for high temperature high pressure polymerization, ethylene and 1-hexene were continuously injected into the reactor, and the total pressure was set at 90 MPa, the 1-hexene concentration at 18 mol % and the hydrogen concentration at 5 mol %. The content in the reactor was stirred at 1,500 rpm, the above obtained polymerization catalyst was continuously supplied from the supply port of the reactor, and polymerization reaction was carried out while the average temperature was kept at 200° C. The obtained linear low density polyethylene LL-4 had MFR=2.0 g/10 min and a density of 907 kg/m$^3$. The results of evaluation of basic properties of LL-4 are shown in Table 1, (2) High Density Polyethylene

HD-1

[Preparation of Modified Clay Compound]

Into a mixed solvent of 3 L of deionized water and 3 L of ethanol, 532 g of dioleylmethylamine $(C_{18}N_{35})_2(CH_3)N$ and 125 g of 37% hydrochloric acid were added to prepare an aqueous dioleylmethylamine hydrochloride solution. The solution was heated to 45° C., and 1,000 g of synthetic hectorite was added, followed by stirring at 60° C. for 1 hour. The obtained reaction solution was subjected to filtration, and the solid content was sufficiently washed with water. The solid content was dried to obtain 1,180 g of organic modified clay compound. As a result of measurement by an infrared moisture meter, the moisture content was 0.8%. The organic modified day compound was jet-ground to adjust the average particle size to be 15 μm,

[Preparation of Polymerization Catalyst]

Into a 5 L flask, 450 g of the organic modified day compound obtained in the item [Preparation of modified day compound] and 1.4 kg of hexane were added, 7.06 kg (18 mmol) of bis(indenyl)zirconium chloride and 1.78 kg (1.8 mol) of a hexane 20 wt % solution of triisobutyl aluminum were added, followed by heating at 60° C. and by stirring for 3 hours. Then, the system was cooled to 45° C. and left at rest for 2 hours, and the supernatant liquid was removed. Then, an operation of adding 1.78 kg (0.09 mol) of a hexane 1 wt% solution of triisobutylaluminum, followed by stirring at 45° C. for 30 minutes, leaving the system at rest for 2 hours and then removing the supernatant liquid, was carried out two times, 0.45 kg (0.45 mol) of a hexane 20 wt % solution of triisobutylaluminum was added, and the mixture was diluted again with hexane to bring the total amount to be 4.5 L thereby to prepare polymerization catalyst.

[Production of HD-1]

Into a polymerization reactor having an internal capacity of 300 L, hexane at a rate of 135 kg/hour, ethylene at a rate of 20.0 kg/hour, hydrogen at a rate of 15 NL/hour, the polymerization catalyst obtained in the item [Preparation of polymerization catalyst], and a hexane 20 wt % solution of triisobutylaluminum as a promotor in an amount to bring the concentration of triisobutylaluminum in the liquid to be 0.93 mmol/kg hexane, were continuously supplied. The polymerization temperature was controlled to be 85° C. The obtained high density polyethylene HD-1 had MFR=5.0 g/10 min and a density of 958 kg/m$^3$. The results of evaluation of basic properties of HD-1 are shown in Table 2.

HD-2

[Preparation of Modified Clay]

Modified clay compound was prepared in the same manner as for HD-1.

[Preparation of Polymerization Catalyst]

Polymerization catalyst was prepared in the same manner as for RD-1.

[Production of HD-2]

Into a polymerization reactor having an internal capacity of 300 L, hexane at a rate of 135 kg/hour, ethylene at a rate of 20.0 kg/hour, hydrogen at a rate of 5 NL/hour, the polymerization catalyst obtained in the item [Preparation of polymerization catalyst], and a hexane 20 wt % solution of triisobutylaluminum as a promotor in an amount to bring the concentration of triisobutylaluminum in the liquid to be 0.93 mmol/kg hexane, were continuously supplied. The polymerization temperature was controlled to be 85° C. The obtained high density polyethylene HD-2 had MFR=1.0 g/10 min and a density of 952 kg/m$^3$. The results of evaluation of basic properties of HD-2 are shown in Table 2.

(3) Linear Low Density Polyethylene

LD-1: The Following Commercial Product was Used.

Manufactured by TOSOH CORPORATION, PETROTHENE 172 (trade name) (MFR: 0.3 g/10 min, density: 920 kg/m$^3$). The results of evaluation of basic properties of LD-1 are shown in Table 3.

LD-2: The following commercial product was used.

Manufactured by TOSOH CORPORATION, PETROTHENE 360 (trade name) (MFR: 1.6 g/10 min, density: 919 kg/m$^3$). The results of evaluation of basic properties of LD-2 are shown in Table 3.

LD-3: The following commercial product was used.

Manufactured by TOSOH CORPORATION, PETROTHENE 176 (trade name) (MFR: 1.0 g/10 min, density: 924 kg/m$^3$). The results of evaluation of basic properties of LD-3 are shown in Table 3.

LD-4: The following commercial product was used.

Manufactured by TOSOH CORPORATION, PETROTHENE 173 (trade name) (MFR: 0.3 g/10 min, density: 924 kg/m$^3$). The results of evaluation of basic properties of LD-4 are shown in Table 3.

LD-5: The Following Commercial Product was Used.

Manufactured by TOSOH CORPORATION, PETROTHENE 175K (trade name) (MFR: 0.6 g/10 min, density: 922 kg/m$^3$). The results of evaluation of basic properties of LD-5 are shown in Table 3.

<Resin Composition>

The above linear low density polyethylene (A), the high density polyethylene (B) and the high pressure low density polyethylene (C) were dry-blended in the proportion as identified in Examples and Comparative Examples, and melt-mixed by a 50 mm single screw extruder manufactured by Placo Co., Ltd. to prepare resin pallets for evaluation. The barrel temperature was 01:180° C., 02:190° C., 03:200° C., 04:200° C., and die head:200° C.

B. Laminate and Sealed Container

The laminate and the medical container used in Examples and Comparative Examples were produced and subjected to sterilization by the following method.

<Production of Laminate and Medical Container>

Using a water cooling three-layer co-extrusion blown film making machine (manufactured by Placo Co., Ltd.), a three-layer film having a film width of 135 mm and a film thickness of 250 μm was produced at a cylinder temperature of 180° C., at a water bath temperature of 15° C., at a drawing rate of 6 m/min. For the outer layer and the inner layer, polyethylene Nipolon-P FY13 (trade name) (MFR: 1.0 g/10 min, density: 950 kg/m$^3$) manufactured by TOSOH CORPORATION was used. The thicknesses of the respective layers were such that the outer layer and the inner layer were 20 μm and the intermediate layer was 210 μm. Then, a sample having a length of 195 mm was cut out from the three-layer film, one edge was heat-sealed to form a bag, which was filled with 300 ml of ultrapure water, and the opening was heat-sealed with 50 ml of a head space to prepare a medical container.
<Sterilization>

The medical container was subjected to sterilization using a steam type sterilizer (manufactured by HISAKA WORKS, LTD.) at a temperature of 121° C. for 20 minutes.

Properties of the resin composition, the laminate and the medical container used in Examples and Comparative Examples were evaluated by the following methods.
<Extrusion Property>

In a case where the resin pressure of the extruder for the intermediate layer at the time of film formation by the water cooling three-layer co-extrusion blown film making machine was at most 20 MPa, the resin composition was evaluated to have favorable extrusion property.

O: Extrusion property good (resin pressure of at most 20 MPa)

x: Extrusion property poor (resin pressure of higher than 20 MPa)
<Forming Stability>

The stability of the film (bubble) at the time of film formation by the water cooling three-layer co-extrusion blown film making machine was visually observed and evaluated, O: Bubble stability good x: Bubble non-uniformity significant
<Transparency>

A test specimen of 10 mm in width×50 mm in length was cut out from each of the three-layer film and the medical container after sterilization, and the light transmittance at a wavelength of 450 nm was measured in pure water using an ultraviolet/visible spectrophotometer (manufactured by Hitachi, Ltd., model 220A). A medical container having a light transmittance of at least 70% maintained after sterilization was evaluated as having favorable transparency.
<Heat Resistance>

Wrinkles on the film surface, deformation, fusion between inner layers, etc. after sterilization were visually evaluated, and a film with no wrinkle nor deformation observed counts 3 point, a film with slight wrinkle or deformation observed counts 2 points, and a film with remarkable wrinkle or deformation observed counts 1 points.

Example 1

Using the resin composition shown in Table 4, a three-layer film was formed by a water cooling co-extrusion blown film making machine, and forming stability, and surface smoothness and transparency of the film were evaluated. The film thickness was 250 μm. The obtained film was heat-sealed and a medical container filled with ultrapure water was prepared, which was subjected to high pressure steam sterilization at 121° C., and with respect to the film after sterilized, outer appearance, transparency, flexibility, moisture permeability and cleanness were evaluated. The evaluation results are shown in Table 4.

Examples 2 to 7 and Comparative Examples 1 to 10

A three-layer film and a medical container were prepared and evaluated in the same manner as in Example 1 except that the resin composition used for the intermediate layer was changed as identified in Table 4 or 5. The evaluation results are shown in Tables 4 and 5.

TABLE 1

| | | Linear low density polyethylene | | | |
| --- | --- | --- | --- | --- | --- |
| | Unit | LL-1 | LL-2 | LL-3 | LL-4 |
| MFR | g/10 min | 4.0 | 5.0 | 7.0 | 2.0 |
| Density | kg/m$^3$ | 910 | 900 | 910 | 907 |
| Mw/Mn | — | — | 2.5 | 2.5 | 2.5 | 2.2 |

TABLE 2

| | | High density polyethylene | |
| --- | --- | --- | --- |
| | Unit | HD-1 | HD-2 |
| MFR | g/10 min | 5.0 | 1.0 |
| Density | kg/m$^3$ | 958 | 952 |
| Mw/Mn | — | 2.9 | 2.8 |

TABLE 3

| | | High pressure low density polyethylene | | | | |
| --- | --- | --- | --- | --- | --- | --- |
| | Unit | LD-1 | LD-2 | LD-3 | LD-4 | LD-5 |
| MFR | g/10 min | 0.3 | 1.6 | 1.0 | 0.3 | 0.6 |
| Density | kg/m$^3$ | 920 | 919 | 924 | 924 | 922 |
| Melt strength | mN | 255 | 295 | 135 | 210 | 180 |

TABLE 4

| | | | | Ex. 1 | Ex. 2 | Ex. 3 | Ex. 4 | Ex. 5 | Ex. 6 | Ex. 7 |
| --- | --- | --- | --- | --- | --- | --- | --- | --- | --- | --- |
| Intermediate layer | Linear low density polyethylene (A) | Grade | — | LL-1 | LL-1 | LL-2 | LL-2 | LL-3 | LL-1 | LL-1 |
| | | MFR | (g/10 min) | 4.0 | 4.0 | 5.0 | 5.0 | 7.0 | 4.0 | 4.0 |
| | | Density | (kg/m$^3$) | 910 | 910 | 900 | 900 | 910 | 910 | 910 |
| | | Blend ratio | (wt %) | 75 | 77 | 75 | 65 | 73 | 75 | 71 |
| | High density polyethylene (B) | Grade | — | HD-1 | HD-1 | HD-1 | HD-1 | HD-1 | HD-1 | HD-1 |
| | | MFR | (g/10 min) | 5.0 | 5.0 | 5.0 | 5.0 | 5.0 | 5.0 | 5.0 |
| | | Density | (kg/m$^3$) | 958 | 958 | 958 | 958 | 958 | 958 | 958 |
| | | Blend ratio | (wt %) | 20 | 20 | 20 | 30 | 17 | 20 | 19 |
| | High pressure low density polyethylene (C) | Grade | — | LD-1 | LD-1 | LD-1 | LD-1 | LD-1 | LD-4 | LD-4 |
| | | MFR | (g/10 min) | 0.3 | 0.3 | 0.3 | 0.3 | 0.3 | 0.3 | 0.3 |
| | | Density | (kg/m$^3$) | 920 | 920 | 920 | 920 | 920 | 924 | 924 |
| | | Blend ratio | (wt %) | 5 | 3 | 5 | 5 | 10 | 5 | 10 |
| | Resin composition | MFR | (g/10 min) | 3.7 | 3.9 | 4.3 | 4.3 | 4.8 | 3.7 | 3.2 |
| | | Density | (kg/m$^3$) | 920 | 920 | 913 | 918 | 919 | 920 | 921 |

TABLE 4-continued

|  |  |  | Ex. 1 | Ex. 2 | Ex. 3 | Ex. 4 | Ex. 5 | Ex. 6 | Ex. 7 |
|---|---|---|---|---|---|---|---|---|---|
| Evaluation results | Extrusion property | — | — | ○ | ○ | ○ | ○ | ○ | ○ |
|  | Forming stability | — | — | ○ | ○ | ○ | ○ | ○ | ○ |
|  | Transparency | (%) | 74 | 75 | 76 | 71 | 75 | 74 | 73 |
|  | Heat resistance | — | 3 | 3 | 3 | 3 | 3 | 3 | 3 |

TABLE 5

| | | | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 |
|---|---|---|---|---|---|---|---|---|---|---|---|---|---|
| Inter-mediate layer | Linear low density polyethylene (A) | Grade | — | LL-4 | LL-4 | LL-2 | LL-2 | LL-2 | LL-2 | LL-2 | LL-2 | LL-1 | LL-1 |
| | | MFR | (g/10 min) | 2.0 | 2.0 | 5.0 | 5.0 | 5.0 | 5.0 | 5.0 | 5.0 | 4.0 | 4.0 |
| | | Density | (kg/m³) | 907 | 907 | 900 | 900 | 900 | 900 | 900 | 900 | 910 | 910 |
| | | Blend ratio | (wt %) | 70 | 70 | 70 | 75 | 70 | 90 | 45 | 55 | 75 | 70 |
| | High density polyethylene (B) | Grade | — | HD-2 | HD-1 | HD-2 | HD-1 | HD-1 | HD-1 | HD-1 | HD-1 | HD-1 | HD-1 |
| | | MFR | (g/10 min) | 1.0 | 5.0 | 1.0 | 5.0 | 5.0 | 5.0 | 5.0 | 5.0 | 5.0 | 5.0 |
| | | Density | (kg/m³) | 952 | 958 | 952 | 958 | 958 | 958 | 958 | 958 | 958 | 958 |
| | | Blend ratio | (wt %) | 30 | 30 | 30 | 20 | 20 | 5 | 50 | 20 | 20 | 30 |
| | High pressure low density polyethylene (C) | Grade | — | — | — | — | LD-2 | LD-3 | LD-1 | LD-1 | LD-1 | LD-5 | — |
| | | MFR | (g/10 min) | — | — | — | 1.6 | 1.0 | 0.3 | 0.3 | 0.3 | 0.6 | — |
| | | Density | (kg/m³) | — | — | — | 919 | 924 | 920 | 920 | 920 | 922 | — |
| | | Blend ratio | (wt %) | — | — | — | 5 | 10 | 5 | 5 | 25 | 5 | — |
| | Resin composition | MFR | (g/10 min) | 1.6 | 2.6 | 3.1 | 4.7 | 4.3 | 4.3 | 4.3 | 2.5 | 3.8 | 4.3 |
| | | Density | (kg/m³) | 921 | 922 | 916 | 913 | 914 | 904 | 930 | 917 | 920 | 924 |
| Evaluation results | | Extrusion property | — | x | x | x | ○ | ○ | ○ | ○ | x | ○ | ○ |
| | | Forming stability | — | ○ | x | x | x | x | ○ | ○ | ○ | x | x |
| | | Transparency | (%) | 75 | — | — | — | — | — | 62 | 67 | — | — |
| | | Heat resistance | — | 3 | — | — | — | — | 1 | 3 | 2 | — | — |

The present invention was described in detail with reference to specific embodiments. However, it is obvious for those skilled in the art that various changes and modifications are possible without departing from the intention and the scope of the present invention.

The entire disclosure of Japanese Patent Application No. 2018-170650 filed on Sep. 12, 2018 including specification, claims, drawings and summary is incorporated herein by reference in its entirety.

The invention claimed is:

1. A polyethylene resin composition comprising from 50 to 89 parts by weight of a linear low density polyethylene (A) which satisfies following requirements (a) to (c), from 10 to 40 parts by weight of a high density polyethylene (B) which satisfies following requirements (d) to (f), and from 1 to 20 parts by weight of a high pressure low density polyethylene (C) which satisfies following requirements (g) to (i) (the total amount of (A), (B) and (C) is 100 parts by weight), and the polyethylene resin composition satisfying following requirement (j) wherein melt mass flow rate (MFR) is measured in accordance with JIS K6922-1 at 190° C. under a load of 21.18N:

(a): density is from 890 to 920 kg/m³,
(b): MFR is from 3.0 to 15 g/10 min,
(c): a ratio of weight average molecular weight (Mw) to number average molecular weight (Mn) (Mw/Mn) is from 2.0 to 3.0,
(d): density is from 935 to 970 kg/m³,
(e): MFR is from 3.0 to 15 g/10 min,
(f): a ratio of weight average molecular weight (Mw) to number average molecular weight (Mn) (Mw/Mn) is from 2.0 to 3.0,
(g): density is from 910 to 930 kg/m³,
(h): MFR is from 0.1 to 1.0 g/10 min,
(i): melt strength is from 200 to 400 mN,
(j): MFR is from 3.0 to 9.0 g/10 min.

2. A laminate of at least three layers comprising layer A, layer B and layer C in this order, wherein the layer B is formed of the polyethylene resin composition as defined in claim 1, and the layers A and C are formed of a thermoplastic resin.

3. The laminate according to claim 2, wherein the thermoplastic resin for the layers A and C is a resin composition containing polyethylene.

4. The laminate according to claim 2, which has a light transmittance of at least 70% after sterilized at 121° C.

5. A medical container comprising the laminate as defined in claim 2.

6. A medical container comprising a compartment to store a chemical solution, wherein at least the compartment comprises the laminate as defined in claim 2.

7. The medical container according to claim 5, which has a light transmittance of at least 70% after subjected to sterilization at 121° C. for 20 minutes.

* * * * *